US012651344B2

(12) United States Patent
    Xie et al.

(10) Patent No.: US 12,651,344 B2
(45) Date of Patent: Jun. 9, 2026

(54) GENERATING IMAGE-BASED BIOMARKERS FOR ALZHEIMER'S DISEASE AND RELATED DEMENTIAS

(71) Applicant: Siemens Healthineers AG, Forchheim (DE)

(72) Inventors: Long Xie, Chesterbrook, PA (US); Eli Gibson, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 265 days.

(21) Appl. No.: 18/409,956

(22) Filed: Jan. 11, 2024

(65) Prior Publication Data

US 2024/0273727 A1     Aug. 15, 2024

(30) Foreign Application Priority Data

Feb. 13, 2023    (EP) ..................................... 23156236

(51) Int. Cl.
    *G06T 7/00*        (2017.01)
    *G06T 7/30*        (2017.01)
    *G06V 10/764*      (2022.01)
    *G06V 10/774*      (2022.01)
    *G06V 10/82*       (2022.01)
    *G16H 30/40*       (2018.01)
    *G16H 50/20*       (2018.01)

(52) U.S. Cl.
    CPC .............. *G06T 7/0016* (2013.01); *G06T 7/30* (2017.01); *G06V 10/764* (2022.01); *G06V 10/774* (2022.01); *G06V 10/82* (2022.01); *G16H 30/40* (2018.01); *G06T 2207/10088* (2013.01); *G06T 2207/10104* (2013.01); *G06T*

*2207/20081* (2013.01); *G06T 2207/20084* (2013.01); *G06T 2207/30016* (2013.01); *G06V 2201/03* (2022.01)

(58) Field of Classification Search
    USPC .................................. 382/128, 131, 156, 159
    See application file for complete search history.

(56) References Cited

U.S. PATENT DOCUMENTS

| | | | | |
|---|---|---|---|---|
| 10,949,973 B2 * | 3/2021 | Kim | ...................... | G06T 7/0016 |
| 11,379,978 B2 * | 7/2022 | Anderson | ............ | G06N 3/0455 |
| 12,400,321 B2 * | 8/2025 | Feng | ................... | A61B 5/0042 |
| 2024/0079143 A1 * | 3/2024 | Lee | ......................... | G16H 30/40 |
| 2024/0225538 A1 * | 7/2024 | Seeley | ................... | G16H 30/40 |

OTHER PUBLICATIONS

Fischl, Bruce. "FreeSurfer." Neuroimage 62.2 (2012): 774-781.
Avants, Brian B., Nick Tustison, and Gang Song. "Advanced normalization tools (ANTS)." Insight j 2.365 (2009): 1-35.
(Continued)

*Primary Examiner* — Ishrat I Sherali

(57) ABSTRACT

Image-based biomarkers are provided for active disease progression of Alzheimer's disease and related dementias (ADRD) by training and using artificial neural networks (ANNs) on the basis of subject's images. A cross-sectional sub-pipeline and a longitudinal sub-pipeline are used for processing different images parts, namely cross-sectional imaging data and longitudinal imaging data. A patch-based multiple instance learning (MIL) scheme is applied.

15 Claims, 6 Drawing Sheets

(56)             References Cited

OTHER PUBLICATIONS

Wolk, David A., et al. "Medial temporal lobe subregional morphometry using high resolution MRI in Alzheimer's disease." Neurobiology of aging 49 (2017): 204-213.

Xie, Long, et al. "Longitudinal atrophy in early Braak regions in preclinical Alzheimer's disease." Human brain mapping 41.16 (2020): 4704-4717.

Yamanakkanavar, Nagaraj, Jae Young Choi, and Bumshik Lee. "MRI segmentation and classification of human brain using deep learning for diagnosis of Alzheimer's disease: a survey." Sensors 20.11 (2020): 3243.

Ilse, Maximilian, Jakub Tomczak, and Max Welling. "Attention-based deep multiple instance learning." International conference on machine learning. PMLR, 2018.

Graves, Alex. "Long short-term memory." Supervised sequence labelling with recurrent neural networks (2012): 37-45.

Bergner, Benjamin, et al. "Interpretable and Interactive Deep Multiple Instance Learning for Dental Caries Classification in Bitewing X-rays." arXiv preprint arXiv:2112.09694 (2021).

Cui Ruoxuan et al: "RNN-based longitudinal analysis for diagnosis of Alzheimer's disease", Computerized Medical Imaging and Graphics, vol. 73, Dec. 31, 2019 (Dec. 31, 2019), pp. 1-10.

Lu Donghuan et al: "Multimodal and Multiscale Deep Neural Networks for the Early Diagnosis of Alzheimer's Disease using structural MR and FOG-PET images", Scientific Reports, vol. 8, No. 1, Apr. 9, 2018 (Apr. 9, 2018).

Khojaste-Sarakhsi Met al: "Deep learning 1-15 for Alzheimer's disease diagnosis: A survey", Artificial Intelligence in Medicine, Elsevier, NL, vol. 130, Jun. 12, 2022 (Jun. 12, 2022).

Anonymous: "Multiple instance learning—1-15 Wikipedia", Aug. 14, 2020 (Aug. 14, 2020), XP055812637, Retrieved from the Internet: URL https://en.wikipedia.org/w/index.php?title=Multiple_instance_1earning&01did=972908596 [retrieved on Jun. 10, 2021].

Extended European Search Report (EESR) mailed Aug. 4, 2023 in corresponding European Patent Application No. 23156236.4.

* cited by examiner

FIG 2

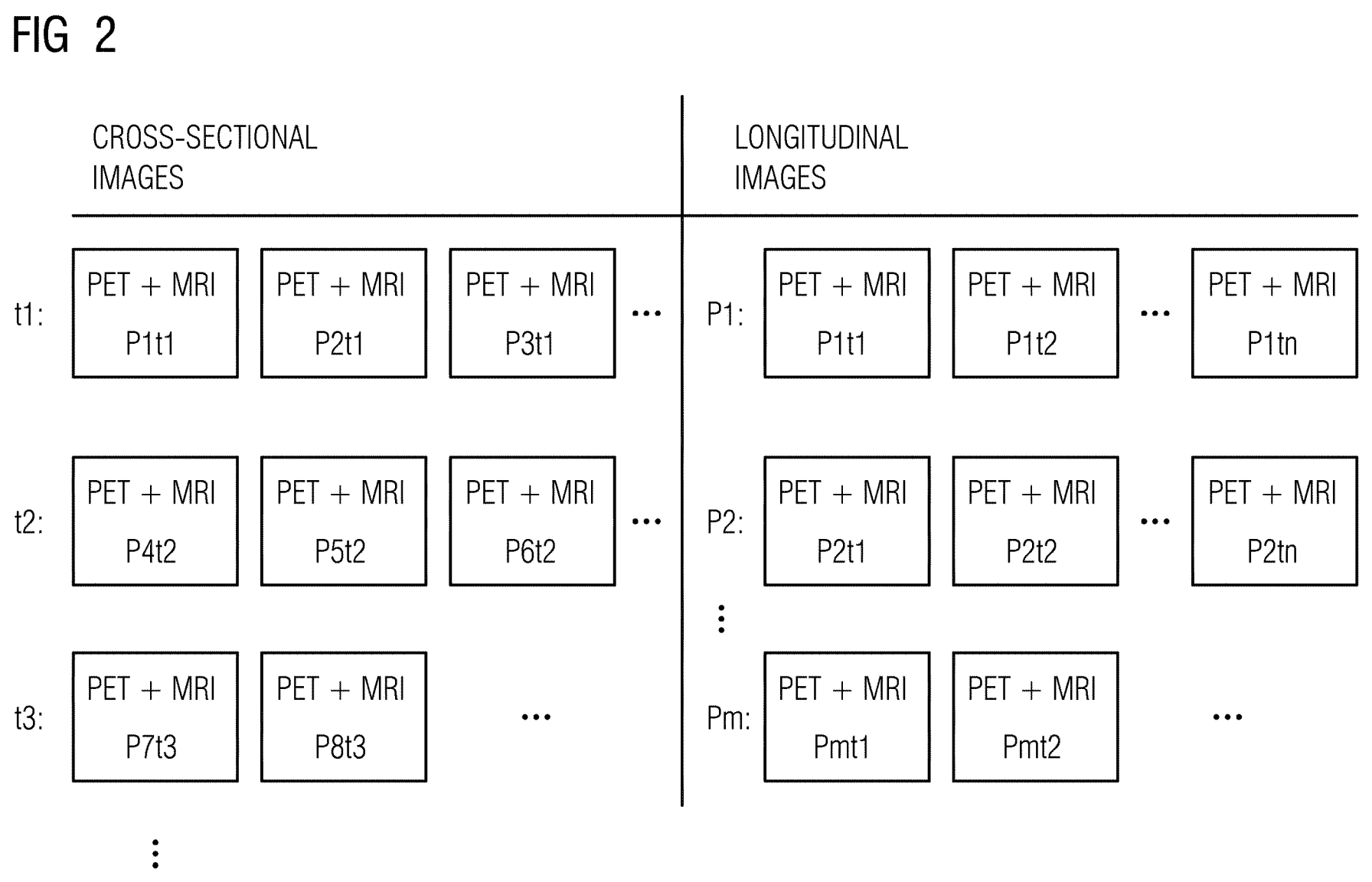

LONGITUDINAL IMAGES

P1:
| PET + MRI P1t1 | PET + MRI P1t2 | ⋮ | PET + MRI P1tn |

P2:
| PET + MRI P2t1 | PET + MRI P2t2 | ⋮ | PET + MRI P2tn |

⋯

Pm:
| PET + MRI Pmt1 | PET + MRI Pmt2 | ⋮ |

CROSS-SECTIONAL IMAGES t1:
| PET + MRI P1t1 | PET + MRI P2t1 | PET + MRI P3t1 | ⋮ | t2:
| PET + MRI P4t2 | PET + MRI P5t2 | PET + MRI P6t2 | ⋮ | t3:
| PET + MRI P7t3 | PET + MRI P8t3 |

⋯

CNN classification network training

Bags of patches in MIL

Multimodal Image patches

Original whole brain image

GENERATING IMAGE-BASED BIOMARKERS FOR ALZHEIMER'S DISEASE AND RELATED DEMENTIAS

This application claims the benefit of EP 23156236.4, filed on Feb. 13, 2023, which is hereby incorporated by reference in its entirety.

FIELD

The present disclosure relates to the field of medical technology and refers to an artificial intelligence (AI) system for generating image-based biomarkers for Alzheimer's disease (AD) and related dementias (ADRD). In particular, the disclosure relates to a training method for training artificial neural networks (ANNs), an inference method for using such trained ANNs, a system for generating image-based biomarkers for active disease progression of Alzheimer's disease and related dementias, a computer program, a computer program product and a non-transitory computer-readable memory.

BACKGROUND

Detecting and/or curing Alzheimer's disease (AD) and related dementias (ADRD) is one of the great challenges of our generation. With the world's growing aging population and the anticipated increasing treatment options in near future, the healthcare market for dementia will grow significantly.

Developing imaging biomarkers based on images, e.g., magnetic resonance imaging (MRI) and positron emission tomography (PET), that are sensitive to AD-related changes is crucial for clinical needs of dementia care and drug development, including differential diagnosis, early identification of AD patients, tracking and staging disease progression, quantifying treatment effects and/or detecting treatment-related adverse effects etc.

However, most of the state-of-the-art imaging biomarkers rely on accurate segmentation of brain structures and detailed registration between longitudinal scans, which are slow and have limited sensitivity to disease-related changes in early phases.

On the other hand, emerging machine learning-based biomarkers suffer from the lack of interpretability and inability in tracking longitudinal disease progression, limiting their clinical utility.

SUMMARY AND DETAILED DESCRIPTION

The object is to provide methods and systems to process image data in order to be able to calculate a reliable prediction on disease or disease progression in a fast manner and also covering an early time phase, which means that it should be possible to have a disease prediction already in early stages of disease development. Image data processing should be provided to provide image-bases biomarkers for diseases of AD and ADRD. Further, the system should be fast at deployment. A major object is also that the system should be capable of processing longitudinal images as well as cross-sectional images. The generated imaging biomarkers should be sensitive to disease-related changes, especially in early phases. Further, a training method and training apparatus as well as an inference method should be provided for such a system as well as a computer program and a respective product and non-transitory storage medium.

According to a first aspect, a computer-implemented method is provided for training artificial neural networks (ANNs) for generating image-based biomarkers for active disease progression, in particular of Alzheimer's disease and related dementias (ADRD) with the following acts:

Receiving at least a pair, preferably, multiple pairs, of images from two different modalities of the same subject at the same timepoint, wherein a subject's imaging data is processed as cross-sectional imaging data, if it is acquired in a cross-sectional setting, in which each subject has only one pair of images acquired at the same timepoint and wherein a subject's imaging data is processed as longitudinal data, if the imaging data is acquired in a longitudinal setting, in which each subject has multiple pairs of images received at different timepoints;

Registering the images, wherein for cross-sectional imaging data: registering is performed between each pair of different modality images at the same timepoint of each subject and wherein for longitudinal imaging data: registering is performed not only between pairs of different modality images at the same timepoint of each subject but also between images of different timepoints of each subject;

Generating a multi-modal dataset, comprising the received images and transformations generated by the registrations, either being cross-sectional or longitudinal;

Extracting multi-modal image patches in a space of the received images, either cross-sectional or longitudinal, based on the generated multi-modal dataset;

Providing a cross-sectional sub-pipeline for processing cross-sectional imaging data and providing a longitudinal sub-pipeline for processing longitudinal imaging data;

When processing cross-sectional imaging data: Training a first ANN system, in particular a convolutional neural network, CNN, by using a patch-based multiple instance learning, MIL, scheme for classifying the extracted multi-modal image patches by predicting a class membership, wherein a class is selected from the group consisting of cognitively normal class, mild cognitive impairment, MCI, class and Alzheimer Disease, AD, class; or When processing longitudinal imaging data: Training a second ANN system, in particular a recurrent neural network, RNN, for generating feature vectors of longitudinal patches with longitudinal disease information, and training another CNN with the patch-based multiple instance learning, MIL, scheme to predict a class membership using the feature vectors generated by the RNN, wherein a class is selected from the group consisting of cognitively normal class, MCI class and AD class; and Providing the trained first and second ANN for generating image-based biomarkers for active disease progression of Alzheimer's disease and related dementias, ADRD.

In general, compared to conventional computational approaches, the above-mentioned suggested solution provides more reliable results, also in early disease phases. Conventional computational approaches are modest at best when it comes to detecting atrophy in early phases of AD, especially in a cross-sectional setting. Cross-sectional volume and shape measures are highly variable, reflecting not only AD-related pathological changes but, perhaps to a greater extent, developmental and other lifespan factors, which are particularly confounding in preclinical AD. In addition, at typical research-grade MRI resolution (e.g., in the range of 1.0-1.3 mm, or even in between 0.1 mm to 1.3 mm) subtle atrophy in preclinical AD may only manifest itself as small partial volume differences that would not be reliably detected by conventional morphometry methods (in particular, the quantitative analysis of size and shape variation of structure in a received image) that are based on segmentation of anatomical structures.

The proposed deep-learning-based data-driven AI system is directed to quantify disease-related alterations in image appearance directly without the need for segmentation and minimal registration and thus could be able to detect subtle changes associated with disease that conventional methods cannot. In addition, by using disease specific loss function, the data-driven biomarker will be more specific to disease-related changes.

In a preferred embodiment, the present disclosure relates to AD and ADRD. However, it is also possible to use this neural network architecture for other diseases and related quantification tasks, in particular, such as tumor detection, disease monitoring and/or microhemorrhage detection. In this case, the classes are adapted to the corresponding disease, e.g., tumor class, mild tumor progression class, no tumor class.

Further, patch-based MIL has not been applied to AD-related image predictions. The AI system described in this disclosure has potential to provide accurate heatmaps for interpretation of AD staging, which is important for clinical translation of AD research. In addition, the proposed pipeline is able to generate longitudinal biomarker for tracking disease progression.

An advantage of the methods and system and further claimed subjects is the ability to detect subtle changes that are in sub-voxel level that are hard to detect with conventional methods.

Training on patches rather than on the whole image forces the ANN(s) or the ANN's system(s) to extract local appearance features that are specific to disease. This allows the pipeline to generate more accurate heatmaps for better interpretation.

The RNN is a component in the longitudinal sub-pipeline and can take in a varying number of longitudinal patches to extract disease relevant features from longitudinal scans.

Moreover, the proposed AI system can generate more sensitive, specific, and interpretable biomarkers for differential diagnosis of dementia, staging of AD and so on. In addition, the longitudinal analysis using patches from original images based on MIL and RNN is unique and shows major processing advantages.

In the following, terms used within this application are defined more specifically.

Images are medical images, in particular of the human brain. The images may be 2D or 3D images. Each image refers to and/or represents parts of a specific subject. The subject may be human being or an animal. The subject may be in healthy or in a disease condition.

The images are acquired by a medical imaging apparatus, also called herein "modality." The modality may be MRI, PET, computer tomography (CT), SPECT or others.

Receiving a pair of images, preferably multiple pairs of images, thus relates to receiving a set of two images. These images are also referred to as "originally received" in contrast to the further states of processed images, like e.g., pre-processed or registered images. Preferably, a pair of MRI and PET image is used. PET imaging is a functional imaging technique that uses radioactive substances known as radiotracers to visualize and measure changes in metabolic processes, and in other physiological activities including blood flow, regional chemical composition, and absorption, here preferably acquired of the human brain or selected regions. MRI is an imaging technique used in radiology to form pictures of the anatomy and the physiological processes of the body. MRI scanners use strong magnetic fields, magnetic field gradients, and radio waves to generate images of the organs in the body.

"Imaging data" is a digital dataset of imaging data for a specific subject. Imaging data, which may be generated, based on the received pair of images or in particular, based on an image of the received pair of images. Typically, imaging data are not identical to the image. Imaging data may be generated from the images by execution of processing acts thereon.

The term "multi-modal" dataset refers to a dataset, including the pair of images acquired with (or at) different imaging modalities. The images in the multi-modal dataset may be registered. However, it is to be noted that the originally received images are stored in the multi-modal dataset in their original form (as they are received) together with a transformation dataset, representing the registration between the received images acquired with or at in different imaging modalities.

Since patches are extracted from the (originally) received images but not the registered images, the multi-modal dataset includes the (originally) received images and the transformations generated by the registrations. The reason why patches are extracted from the (originally) received images is to maximally retain the information from images. The resample act in registration will smooth the images and thus disease-related information may be lost.

Transformations may also be denoted herein as "transformation dataset". The transformations or the transformation dataset is the result of the registration procedure, in particular executed algorithmically. The transformation is stored in a memory. Generally, image registration relates to the process of aligning two or more images of the same subject or the same timepoint. In order to align these images, a transformation must be applied to two or more of the images. There are different types of transformations that can be used in image registration. The type may be selected from the group of: translation, rotation, scaling, affine transformation and non-linear transformation. The optimal type of transformation depends on the application. In general, linear transformations, i.e., translation, rotation, scaling, affine transformations, are used to register imaging data from the same subject, and non-linear transformation is applied to register imaging data from different subjects. The transformation is derived by solving an optimization problem to minimize the dissimilarity between the registered image and the target image. Different metrics have been proposed to evaluate the similarity of a pair of images, including sum of square difference, normalized cross-correlation, mutual information and so on.

The images of the pair are acquired by different modalities, e.g., between MRI and PET, taken from the same subject at the same timepoint. Alternatively, also other modalities may be used, such as CT, SPECT, and other emerging medical imaging modalities. Because the images of the pair are acquired by different modalities, the images as such may also be named as multi-modal images.

In the cross-sectional setting, there may be a set of cross-sectional imaging data or image-pairs (from different modalities), received for different subjects wherein each subject has one image or image pair. Cross-sectional imaging data may stem from a cross-sectional setting or study. A cross-sectional study is a type of observational study that involves collecting data from a sample of subjects (e.g., patients or healthy persons) at one point in time for each subject. The goal is typically to examine the relationship between one or more independent variables and one or more dependent variables in a population. This type of study is often used to identify risk factors or to describe the prevalence of a particular condition or disease in a population. It is relatively quick and inexpensive to conduct compared to longitudinal studies.

For example, in the cross-sectional setting, there may be processed data, like e.g.: a first multi-modal dataset {PET+MRI image of subject (who may be a patient) P1 at timepoint P1$t$1} and a second multi-modal dataset may be the pair of: {PET+MRI image of subject P2 at (same) timepoint P2$t$1} and a third multi-modal dataset in the cross-sectional setting may be an image pair of: {PET+MRI image of subject P3 at (same) timepoint P3$t$1} so on and so forth. In cross-sectional setting, every subject, in particular patient, only has one timepoint. In cross-sectional setting, multi-modal image-pair of each subject were received at the same timepoint. With other words, images are processed as cross-sectional images if the images relate to each single subject, acquired at the same timepoint. Moreover, in the cross-sectional setting, sets of images or image pairs from different subjects may be available and processed for different time-points. In particular, each subject only has data from one timepoint but data from different subjects may come from different timepoints.

In the longitudinal setting, there may be a set of longitudinal imaging data or image-pairs (from different modalities), received for the different subjects wherein each subject can have multiple images or image-pairs at different timepoints. A longitudinal study is a type of observational study that involves repeatedly measuring one or more variables of interest in the same subjects over time. The goal is typically to examine how a particular variable changes over time, or to identify factors that predict or influence change. This type of study can provide information about the natural history of a condition or disease, and can help to identify early markers of risk or progression of disease, like e.g., AD and/or ADRD. Longitudinal studies can be costly and time-consuming to conduct, but they can also provide a more detailed understanding of the variables under investigation.

For example, in the longitudinal setting, there may be processed data, like e.g.: a first multi-modal dataset in the longitudinal setting for three different timepoints may be the image pair of: {PET+MRI image of patient P1 at timepoint P1$t$1} and a second multi-modal dataset may be the image pair of: {PET+MRI image of (same) patient P1 at (different) timepoint P1$t$2} and a third multi-model dataset may be image pair of: {PET+MRI image of (same) patient P1 at (different) timepoint P1$t$3}.

Moreover, in the longitudinal setting, different sets of image pairs may be available and processed for different patients. So, a fourth multi-model dataset may be image pair of: {PET+MRI image of (another) patient P2 at timepoint P2$t$1} and a fifth multi-modal dataset may be an image pair of: {PET+MRI image of (same) patient P2 at timepoint P2$t$2} and so on and so forth. So, for longitudinal images or in the longitudinal setting, we have a pair of multi-modal images at each timepoint. For example, if we have a subject, in particular a patient, with data from two timepoints, we have four images. So, if we have two subjects, in particular two patients, with data from two timepoints, we have eight images. The number of timepoints for different subjects, in particular patients, may be different.

In longitudinal setting, the images of different pairs not only differ with respect to the timepoint but may alternatively, or in addition differ with respect to the subject. In other words, in the longitudinal setting, each subject will have multiple pairs of images at different timepoints, in particular more than 1 timepoint. In addition, there will be data for multiple subjects. Longitudinal data or the longitudinal setting allows for the assessment of progression of brain changes over time or over multiple imaging timepoints. With other words, images are processed as longitudinal images if the images relate to the same subject, acquired or received at different timepoints.

Preferably, the act of registering in the longitudinal setting may include registering between images of the same subject (at different timepoints). In addition, registering in the longitudinal setting may include registering between images at the same timepoint.

However, both, in the cross-sectional setting and in the longitudinal setting, there will be processed different sets of images or image-pairs. In particular, in the cross-sectional setting, sets of images or image-pairs are processed from multiple subjects (each subject has data from one timepoint) and/or in the longitudinal setting, sets of images or image-pairs are processed from multiple subjects and multiple timepoints (each subject can have imaging data from multiple timepoints.

Registering relates to compute or perform a registration. This may preferably be done by registration algorithms. Registering the images refers to a digital process of generating an association in time and/or space.

Registering may be applied for both images of a pair of images, stemming from different modalities. The images to be registered may be acquired at a corresponding or common timepoint for the same subject at different modalities.

Registration may also be applied for images in the cross-sectional and/or in the longitudinal setting.

All registrations are done between images of the same subject. There is no between-subject registration done in this solution.

In the cross-sectional setting, registration will be executed between images of modalities of a same subject at the same timepoint.

In addition, or alternatively, in particular in the longitudinal setting, registration may be executed between images or image-pairs of the same subject at different timepoints.

Registration will typically not be done between subjects. Registrations will be done between images of different modalities at the same timepoint (cross-sectional setting) or images of different modalities between different timepoints of a same subject (longitudinal setting).

Registering may be executed by using computerized algorithms to derive a transformation that can relate position of features in one image to the corresponding features in another image. Commonly, linear transformation (translation, rotation, scaling, affine) computed by gradient descent or artificial neural network is used to align multi-modal images (e.g., between PET and MRI or MRI and CT) and non-linear transformation is used to align images of the same subject acquired at different timepoints (e.g., MRI images at different timepoints).

Registering cross-sectional images may relate to generating an association of images from different modalities of the same subjects at the same timepoint. E.g., PET images are registered to the corresponding MRI images at the same time point for the same subject.

"Timepoint" in this context relates to a time phase or time interval. The smallest unit may be a day. However, it is also possible to extend the "timepoint" over a day margin so that images, acquired at different days but at least with the same "period" may serve as images of the same timepoint. The "period" should be in the range of several days and should not extend over half a year. So, for example, a first image, acquired on a certain day in the morning and a second image, acquired on the same day in the evening may be computed as images acquired at the same timepoint. Also, for example, a first image, acquired on a certain day, and a second image, acquired one month later, may be computed as images acquired at the same timepoint. The period of a timepoint is preferably configurable.

Extracting multi-modal image patches may relate to generating an extracted dataset. This is done by cropping or cutting-out small corresponding 2D or 3D regions from multi-modal images at the space of the (originally) received images. Cropping in this context refers to the process of removing unwanted parts of an image and keeping only the desired region of interest. This can be done by defining a rectangular (or irregular) region of the image and discarding the pixels outside of this region. Cropping is used to focus on a specific area in the image. For each multi-modal image pair, more than one patch is extracted. Usually this extracted dataset is more compressed but contains all relevant information for disease evaluation and in particular disease progression.

A patch may be a rectangular or quadratic (for 2D) or cube (for 3D) part of the received image. Typically, several such patches are generated for one single received image. Preferably, the received image is a 3D image and the extracted patches are 3D patches. The patch volume may range in between 125 mm³ to 1000 mm³ and preferably is selected by 512 mm³. In a preferred embodiment, the patch volume may be configurable, at least in the training phase. This has the advantage, that the method and system is better adaptable to the anatomical structures, to be examined and evaluated.

As the present approach is based on an AI system, there is a training phase for training the ANNs and an inference phase, in which the trained ANNs are applied and used. In the inference phase, the method/system/pipeline only will receive or take-in images pairs of the same subject, either cross-sectionally or longitudinally. This is different from that in the training phase. In the training phase, imaging data from multiple subjects is used to train the ANNs.

The solution described herein, uses a patch-based multiple instance learning (MIL) technique or scheme, which is a type of machine learning technique that is used to classify instances (e.g., images, signals, etc.) based on their local features, rather than global features. In patch-based MIL, the input instances are divided into small (overlapping or non-overlapping) patches, and each patch is considered as an individual instance. The goal of the model is to classify each patch as positive or negative, and then to aggregate the patch-level predictions to make a final decision about the entire input instance. So, the model is trained to recognize objects in each patch. The main advantage of patch-based MIL is that it can handle data with significant variability and noise, as it allows the model to focus on the most informative regions of the input instances. It also allows the model to learn from a larger number of positive examples, as the same input instance can be divided into multiple positive patches.

In some MIL algorithms, the patches are typically defined as non-overlapping regions of the input image. This allows the algorithm to learn different features of the image in different regions, but it may lead to the loss of information if the regions of interest are not captured by these patches.

According to a preferred embodiment, however, MIL algorithms are applied, which are based on overlapping patches. This allows the algorithm to learn features from overlapping regions, which can improve the robustness of the algorithm. Additionally, overlapping patches allow for more efficient processing as it can make use of already processed information.

The MIL scheme is only used in training to improve the accuracy of the CNNs. In inference, the trained CNN is applied to the cross-sectional patches to generate the prediction. All the predictions of patches from the same subject will then be unified to generate subject level prediction and heatmap. Also, in inference, the trained CNN and RNN are applied to the longitudinal patches to generate the prediction.

In the longitudinal setting (meaning: processing longitudinal imaging data), the ANN or ANN system, in particular, the RNN and the CNN will be trained. The RNN serves as a feature extraction act to extract longitudinal features, which will be fed into a CNN to perform classification.

In cross-sectional setting, no RNN is needed, because there is only data from single timepoint. The CNN will take the raw image patches as input.

The convolutional neural network (CNN) is a class of artificial neural network (ANN), applied to analyze visual imagery. A CNN may include three main types of layers:

Convolutional layers: apply a set of filters to the input image, to extract local features such as edges, textures, and patterns. The filters are learned during the training process, and they are designed to detect specific features in the input data.

Pooling layers: reduce the spatial resolution of the feature maps, while preserving the most important information. This helps to reduce the computational complexity of the model, and to make it more robust to small translations of the input.

Fully connected layers: process the information from the previous layers, to make predictions about the input. These layers are similar to the layers in a traditional neural network, and they use backpropagation to learn the weights of the model.

In any feed-forward neural network, any middle layers are called hidden because their inputs and outputs are masked by the activation function and final convolution. In a convolutional neural network, the hidden layers include layers that perform convolutions. Typically, this includes a layer that performs a dot product of the convolution kernel with the layer's input matrix. This product is usually the Frobenius inner product, and its activation function is commonly ReLU. As the convolution kernel slides along the input matrix for the layer, the convolution operation generates a feature map, which in turn contributes to the input of the next layer. This is followed by other layers such as pooling layers, fully connected layers, and normalization layers.

For more details to the CNNs used herein it is referred to Heaton, J. Ian Goodfellow, Yoshua Bengio, and Aaron Courville: Deep learning. Genet Program Evolvable Mach 19, 305-307 (2018). https://doi.org/10.1007/s10710-017-9314-z.

The recurrent neural network (RNN) is also a class of ANNs. RNNs are a type of neural network that are particularly well-suited for processing sequential data, such as time series (e.g., of images). RNNs have a "memory" in the form of hidden states, which allows them to maintain information about previous inputs while processing new inputs. RNNs have a structure that repeats itself over time with a feedback connection, so the output of a hidden layer at time t is fed back as input to the same layer at time t+1. The recurrent connections allow the network to maintain a hidden state that encodes information about the context of the input sequence up to that point. Different types of RNNs may be used, such as:

Simple RNN: has a single recurrent connection between the hidden and output layers; or Long Short-Term Memory (LSTM): a more complex RNN architecture that uses gating mechanisms to control the flow of information through the hidden states or Gated Recurrent Unit (GRU): similar to LSTM, but with fewer parameters.

In an embodiment, a long short-term memory (LSTM) may be applied. For more details to RNNs, it is referred to Graves, Alex. "Long short-term memory." Supervised sequence labelling with recurrent neural networks (2012): 37-45.

RNNs exhibit temporal dynamic behavior. Derived from feedforward neural networks, RNNs can use their internal state (memory) to process variable length sequences of inputs. Recurrent neural networks are theoretically Turing complete and can run arbitrary programs to process arbitrary sequences of inputs.

The first ANN, in particular the first CNN, is used for processing cross-sectional images. It serves to generate the result dataset with the class prediction from input data, in particular from bags of patches.

The second ANN, in particular the second CNN, is used for processing longitudinal images. It serves to generate the result dataset with the class prediction from input data, in particular from bags of feature vectors extracted by the RNN.

The RNN is used for processing longitudinal images. The RNN takes-in input data, in particular, multi-modal image patches, more specifically, multi-modal image patches of longitudinal images and generates features used by the second CNN to perform class prediction.

The result dataset is a digital dataset which may be provided on the output interface (e.g., on a user interface) and/or may be processed digitally and/or may be transferred to other computing entities via communication links (wired or wireless).

The cognitively normal class may refer to subjects with a normal state of cognition. The subject may be healthy or may have other diseases apart from cognitive impairments.

The MCI class relates to subjects with mild cognitive impairment. This class is in the intermediate stage, between persons without cognitive impairment and persons with severe cognitive impairment due to Alzheimer disease or related dementia.

The AD class relates to subjects with any kind of Alzheimer disease or related diseases, which may be representable in brain structures.

For other diseases, the classes are chosen correspondingly (disease class, mild symptoms class, healthy class).

The cross-sectional sub-pipeline may include one ANN, in particular a CNN. Alternatively, or in addition, the cross-sectional sub-pipeline may use a patch-based multiple instance learning scheme (MIL).

The longitudinal sub-pipeline may include two different ANNs, in particular an RNN and a second CNN (different from the CNN of the cross-sectional pipeline, mentioned before). The RNN is used as a preceding module or act for generating feature vectors of longitudinal patches with longitudinal disease information. The CNN is then used to predict the class membership.

The cross-sectional sub-pipeline and the longitudinal sub-pipeline are not symmetric and have a different architecture.

Alternatively, or in addition, the received images may be subject to pre-processing. The pre-processing may include generating a registration dataset by registering different images, extracting patches and/or re-organizing the patches into bags of patches.

Alternatively, or in addition, a cross-entropy loss may be used as a loss function. In artificial intelligence, a loss function (also known as a cost function or objective function) is a mathematical function that measures the difference between the predicted output and the true output of a model. The goal of training an AI model is to find the parameters that minimize the loss function. The loss function is typically chosen based on the type of problem being solved and the type of model being used. In an embodiment, the cross-entropy loss is used. The loss function's value is calculated for each example during the training process, and the model parameters are updated in a way that reduces the total loss value. The training process stops when the loss function values stop decreasing or converge to a minimum value. The choice of loss function is important because it determines the properties of the model, and the optimization algorithm tries to minimize the loss function to get the desired results.

Alternatively, or in addition, —when training the CNN in the cross-sectional and/or longitudinal sub-pipelines—the patch-based MIL scheme re-organizes the patches into bags and assigns a class or a label to each bag, wherein the class is selected from the group consisting of cognitively normal class, MCI class and AD class.

Alternatively, or in addition, the trained CNN and/or the trained RNN are trained on patches rather than on whole images.

Alternatively, or in addition, —when processing longitudinal images—the longitudinal sub-pipeline does not directly extract volume change from a deformation field.

In another aspect, the approach relates to an inference method to be used in an inference phase for generating image-based biomarkers for active disease progression, in particular of Alzheimer's disease and related dementias (ADRD) with the following acts:

Receiving at least a pair of images from two different modalities of the same subject at the same, wherein a subject's imaging data is processed as cross-sectional imaging data, if it is acquired in a cross-sectional setting, in which each subject has only one pair of images acquired at the same timepoint and wherein a subject's imaging data is processed as longitudinal imaging data, if the imaging data is acquired in a longitudinal setting, in which each subject has multiple pairs of images received at different timepoints;

Registering the images, wherein for cross-sectional images: registering is performed between images at the same timepoint and wherein for longitudinal images: registering is performed between images of the same subject, optionally in the longitudinal setting registering between images of the same subject may be performed in addition to registering between images at the same timepoint;

Generating a multi-modal dataset, including the received images and the transformations generated by the registrations, either cross-sectional or longitudinal;

Extracting multi-modal image patches in a space of the received images, either cross-sectional or longitudinal, based on the generated multi-modal dataset;

Providing a cross-sectional sub-pipeline for processing cross-sectional imaging data and providing a longitudinal sub-pipeline for processing longitudinal imaging data;

When processing cross-sectional imaging data: Using a first trained ANN system, in particular a convolutional neural network, CNN, which has been trained with corresponding acts of a method as described above for classifying the extracted multi-modal images patches by predicting a class membership, wherein a class is selected from the group consisting of cognitively normal class, mild cognitive impairment, MCI, class and Alzheimer Disease, AD, class; or When processing longitudinal imaging data: Using a second ANN system, in particular a recurrent neural network, RNN, which has been trained with corresponding acts of a method as described above for generating feature vectors of longitudinal patches with longitudinal disease information, and using another trained CNN to predict a class membership, wherein a class is selected from the group consisting of cognitively normal class, MCI class and AD class; and Providing a predicted class membership as result dataset on an output interface, wherein the result dataset serves as image-based biomarker for active disease progression of Alzheimer's disease and related dementias, ADRD.

In the longitudinal setting: The prediction is still done by a CNN but using features generated by the RNN in longitudinal pipeline. This is different from the cross-sectional pipeline, in which the CNN uses the raw multi-modal image patches.

Alternatively, or in addition, a heatmap is provided as result dataset on the output interface in addition to the predicted class membership. A heatmap is based on a digital processing of data to automatically calculate a representation of data in the form of a map or diagram in which data values are represented as colors.

Alternatively, or in addition, —when processing cross-sectional imaging data—the cross-sectional sub-pipeline at least the following acts are executed:

Registering the images of a first modality with the corresponding images of a second modality from the same subject at the same timepoint to generate a multi-modal dataset of images and a transformation dataset between them;

Extracting patches of the generated multi-modal dataset;

Using the first trained CNN to assign a class label for each of the extracted patches;

Using average predictions of all the patches to determine a subject-level class prediction; and Assembling model outputs of all individual patches into a heatmap indicating the most informative regions for the prediction, serving as evidence for interpretation.

Alternatively, or in addition, —when processing longitudinal imaging data—the longitudinal sub-pipeline at least the following acts are executed:

Registering the images of a first modality with the corresponding images of a second modality from the same subject at each of the timepoints;

Registering the images of the first timepoint (baseline timepoint) to the other timepoints from the same subject;

Generating a multi-modal dataset of received images and a transformation dataset, generated by the registrations;

Extracting multi-modal patches from the baseline timepoints of the multi-modal dataset as baseline patches (BasePAT);

Identifying corresponding patches of the other timepoints in multi-modal datasets for each baseline patch (BasePAT) using a corresponding transformation dataset, derived from registration;

Extracting spatially corresponding patches in their original image space of images from each timepoint, including the baseline and other timepoints, to generate a series of longitudinal images patches for each subject, in particular, one series for each BasePAT;

Feeding the patches, stemming from the longitudinal images, to the trained RNN to generate the feature vectors with longitudinal disease information, wherein the RNN has been trained with a training method according to any of the approaches herein;

Feeding the feature vector to the second trained CNN to generate class prediction;

Using average predictions of all the BasePAT patches to determine subject-level class prediction; and Assembling model outputs of all individual patches into a heatmap indicating the most informative region for the prediction, serving as evidence for further processing, in particular interpretation.

Registering here again means to execute a registration algorithm for providing a registered dataset (in short: a registration).

"Original image space" relates to the image space of the originally received images.

Up to now, the disclosure has been described with respect to the method for training and an inference method, to be executed in an inference phase, after the ANNs have been trained and/or tested. In the following, the solution will be described with respect to the computing device or apparatus and system. Features, advantages or alternative embodiments herein can be assigned to the other claimed objects (e.g., the computer program or a computer program product), and vice versa. In other words, claims for the computing device and system can be improved with features described or taught in the context of the methods. In this case, the functional features of the respective method are embodied by structural units of the system or apparatus and vice versa, respectively.

According to another aspect, a training apparatus is provided for training artificial neural networks (ANNs) for generating image-based biomarkers for active disease progression, in particular of Alzheimer's disease and related dementias (ADRD), which is configured for executing a (training) method as described above, with:

A reception interface (receiver or input interface) is configured for receiving at least a pair of images from two different modalities of the same subject at the same timepoint, wherein a subject's imaging data is processed as cross-sectional imaging data, if it is acquired in a cross-sectional setting, in which each subject has only one pair of images acquired at the same timepoint and wherein a subject's imaging data is processed as longitudinal imaging data, if the image is acquired in a longitudinal setting, in which each subject has multiple pairs of images received at different timepoints; and A computing unit (processor or computer) configured to:

Register the images, wherein for cross-sectional imaging data: registering is performed between images at the same timepoint and wherein for longitudinal images: registering is additionally performed between images of the same subject;

Generate a multi-modal dataset, including the received images and transformations generated by the act of registering, either being cross-sectional or longitudinal;

Extract multi-modal image patches in a space of the received images, either cross-sectional or longitudinal, based on the generated multi-modal dataset;

Provide a cross-sectional sub-pipeline for processing cross-sectional imaging data and providing a longitudinal sub-pipeline for processing longitudinal imaging data;

When processing cross-sectional images: Train a first ANN system, in particular a convolutional neural network (CNN) by using a patch-based multiple instance learning (MIL) scheme for classifying the extracted multi-modal image patches by predicting a class membership, wherein a class is selected from the group consisting of cognitively normal class, mild cognitive impairment (MCI) class and Alzheimer Disease (AD) class; or When processing longitudinal images: Train a second ANN system, in particular a recurrent neural network (RNN) for generating feature vectors of longitudinal patches with longitudinal disease information, and training another CNN with the patch-based multiple instance learning (MIL) scheme to predict a class membership using the feature vectors generated by the RNN, wherein a class is selected from the group consisting of cognitively normal class, MCI class and AD class; and An output interface configured to provide the trained first and second ANN for generating image-based biomarkers for active disease progression of Alzheimer's disease and related dementias (ADRD).

According to another aspect, a system is provided for generating image-based biomarkers for active disease progression, in particular of Alzheimer's disease and related dementias (ADRD), including:

A reception interface, which is configured to receive at least a pair of images from two different modalities of the same subject at the same timepoint, wherein a subject's imaging data is processed as cross-sectional imaging data, if it is acquired in a cross-sectional setting, in which each subject has only one pair of images acquired at the same timepoint and wherein a subject's imaging data is processed as longitudinal imaging data, if the image is acquired in a longitudinal setting, in which each subject has multiple pairs of images received at different timepoints;

A computing unit, which is configured to:

Register the images, wherein for cross-sectional imaging data: registering is performed between images at the same timepoint and wherein for longitudinal imaging data: registering is performed between images of the same subject and may optionally be performed in addition to registering between images at the same timepoint;

Generate a multi-modal dataset, including the received images and transformations generated by the registrations, either being cross-sectional or longitudinal;

Extract multi-modal image patches in a space of the received images, either cross-sectional or longitudinal, based on the generated multi-modal dataset;

Provide a first interface to a cross-sectional sub-pipeline for processing cross-sectional imaging data and providing a second interface to a longitudinal sub-pipeline for processing longitudinal imaging data;

When processing cross-sectional imaging data: Use a first trained ANN system, in particular a convolutional neural network, CNN, which has been trained with corresponding acts of a method as mentioned above for classifying the extracted multi-modal images patches by predicting a class membership, wherein a class is selected from the group consisting of cognitively normal class, mild cognitive impairment, MCI, class and Alzheimer Disease, AD class; or When processing longitudinal imaging data: Use a second ANN system, in particular a recurrent neural network, RNN, which has been trained with corresponding acts of a method as mentioned above for generating feature vectors of longitudinal patches with longitudinal disease information, and using another trained CNN to predict a class membership, wherein a class is selected from the group consisting of cognitively normal class, MCI class and AD class; and An output interface to provide a predicted class membership as result dataset, wherein the result dataset serves as image-based biomarker for active disease progression of Alzheimer's disease and related dementias, ADRD.

In inference, the trained CNN and RNN are applied to the longitudinal patches to generate the prediction. All the predictions of patches from the same subject (e.g., patient) may then be unified to generate subject-level prediction and heatmap.

A "computing unit" may be understood to mean, for example, a computing machine for digital data processing or an electronic circuit. In particular, a computing unit may include a processor, which may be a central processing unit (CPU), a microprocessor or a microcontroller, for example, an application-specific integrated circuit or a digital signal processor, possibly in combination with a memory unit for storing program instructions, etc. A processor may also be, for example, an IC (integrated circuit), in particular an FPGA (field programmable gate array) or an ASIC (application-specific integrated circuit), or e.g., a multi-chip module, e.g., a 2.5D or 3D multi-chip module, in which in particular several so-called dies are connected to one another directly or via an interposer, or a DSP (Digital Signal Processor) or a GPU (Graphic Processing Unit). A processor can also be a virtualized processor, a virtual machine or a soft CPU. It can also be, for example, a programmable processor which is equipped with configuration acts for carrying out the said method according to the invention or is configured with configuration acts in such a way that the programmable processor implements the features according to the invention of the method, the component, the modules, or other aspects and/or partial aspects of the invention.

The first and/or second interface may be an internal interface so that the cross-sectional sub-pipeline and/or the longitudinal sub-pipeline are locally installed in the system's computing unit.

Alternatively, or in addition, the first and/or second interface may be an external interface so that the cross-sectional sub-pipeline and/or the longitudinal sub-pipeline are not provided locally but are accessible via network connection (wired or non-wired, e.g., via internet).

Alternatively, or in addition, the multi-modal dataset is a set, in particular a pair, of images, which have been acquired by different modalities. The images may be cross-sectional images or longitudinal images which may be processed by one and the same inference method or system.

In another aspect, a computer program product includes a computer program, wherein the computer program is loadable into a memory unit (memory) of a computing unit, including program code sections to make the computing unit execute the method for training an ANN as mentioned above or for the inference method as mentioned above, when the computer program is executed in said computing unit.

The computer program product may also be provided for download, e.g., via a radio or cellular network, the Internet and/or a host computer. Alternatively, or in addition, the method may be encoded in a Field-Programmable Gate Array (FPGA) and/or an Application-Specific Integrated Circuit (ASIC), or the functionality may be provided for download by a hardware description language.

In another aspect, a computer program is loadable into a memory unit of a computing unit, including program code sections to make the computing unit execute the method for training an ANN as mentioned above or for the inference method as mentioned above, when the computer program is executed in said computing unit.

In another aspect, a non-transitory computer-readable medium, on which program code sections of one or more computer programs are stored or saved, is provided. Said program code sections are loadable into and/or executable in a computing unit to make the computing unit execute training an ANN as mentioned above or for the inference as mentioned above, when the computer program is executed in said computing unit.

The properties, features and advantages of this invention described above, as well as the manner they are achieved, become clearer and more understandable in the light of the following description and embodiments, which will be described in more detail in the context of the drawings. This following description does not limit the invention on the contained embodiments. Same components or parts can be labelled with the same reference signs in different figures. In general, the figures are not for scale.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

FIG. 2 depicts a structural figure of images of a cross-sectional sub-pipeline and a longitudinal sub-pipeline according to an exemplary embodiment;

DETAILED DESCRIPTION OF THE DRAWINGS

Figure 1:
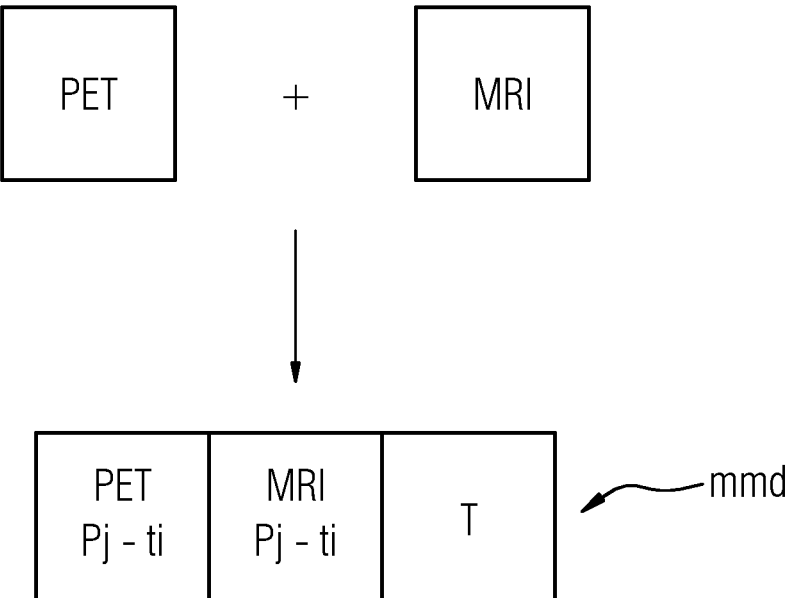
FIG. 1 shows images to be received and a multi-modal dataset according to an embodiment.

FIG. 1 shows a structural representation of two images, which are received and which have been acquired by two different modalities. In this exemplary case, on the left side is a PET image and on the right side is an MRI image. These images may be grouped together as a pair of images.

A multi-modal dataset mmd may be generated, which includes the PET image and the MRI image and a transformation dataset, representing the transformation between the before mentioned images.

The images of the pair of images in the multi-modal dataset mmd typically refer the same patient Pj and the same timepoint ti in which the image has been acquired; therefore in FIG. 1 the PET image is shown as PET Pj-ti and the MRI image is shown as MRI Pj-ti.

FIG. 2 shows a structural representation of images taken from a cross-sectional setting or study on the left-hand side and images taken from the longitudinal setting or study on the right-hand side.

As can be seen on the left side, in a cross-sectional setting, the images or the image pairs belong to different subjects, in particular patients, but relate to the same point of acquisition or timepoint. In other words, images taken in a cross-sectional setting differ from subject to subject (as can be seen in FIG. 2 for the first timepoint t1: P1-t1, P2-t2, P3-t3, . . . ).

However, in a cross-sectional setting, there may be multiple sets (also mentioned herein as "series") of images or image pairs, which each differ in the timepoint, which is the date of acquisition, wherein in each of the set, the images or the image pairs only differ with respect to the subject but may belong to the same or a non-overlapping timepoint. The sets or series are depicted in FIG. 2 in rows. The images of the series, shown in the first row, have been acquired by timepoint t1. The images of the series, shown in the second row, have been acquired at timepoint t2 etc. Different series are processed.

In the cross-sectional setting, images in one "row" (same timepoint) may be registered.

In the figures, in particular in FIG. 2, the reference numeral P refers to a specific patient and the reference numeral t relates to a specific timepoint. For example, P1, relates to a first patient, P2 relates to a second patient, P3 relates to the third patient.

As can be seen on the right-hand side, in the longitudinal setting, the images or image pairs in one set or series correspond to each other with respect to the specific patient and differ in one set or series, which is represented in FIG. 2 as row, in the timepoints. For example in the first set or series, depicted in the first row, all the images relate to the first patient P1, but the images or image pairs are acquired at different timepoints t1, t2, . . . tn. The multi-modal image pairs in the longitudinal setting in FIG. 2 are therefore mentioned as P1t1, P1t2, P1tn in the first row (for images of the first patient P1) and in the second row P2t1, P2t2, . . . , and P2tn.

As can be seen, also in the longitudinal setting, there are different sets or series of images or image pairs, which are processed and wherein each of the sets refers to a specific patient.

In the longitudinal setting, the images in one "row" (same patient or subject) may be registered. Alternatively, in the longitudinal setting, images of or between the same subject may be registered in addition to registering imaging for the same subject.

All the image pairs of the different sets in the longitudinal setting and/or in the cross-sectional setting are processed by the artificial neural networks to generate image-based bio-markers for active disease progression. The methods and systems, presented herein may preferably be used for Alzheimer's disease and related dementias.

Figure 3:
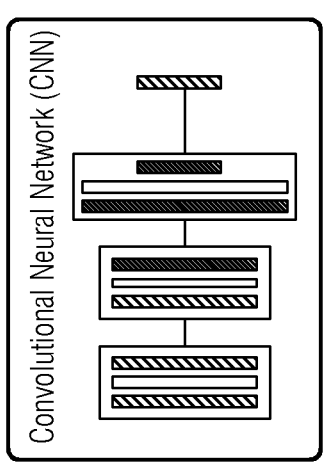
FIG. 3 shows an example cross-sectional sub-pipeline in a schematic representation.
Figure 3:
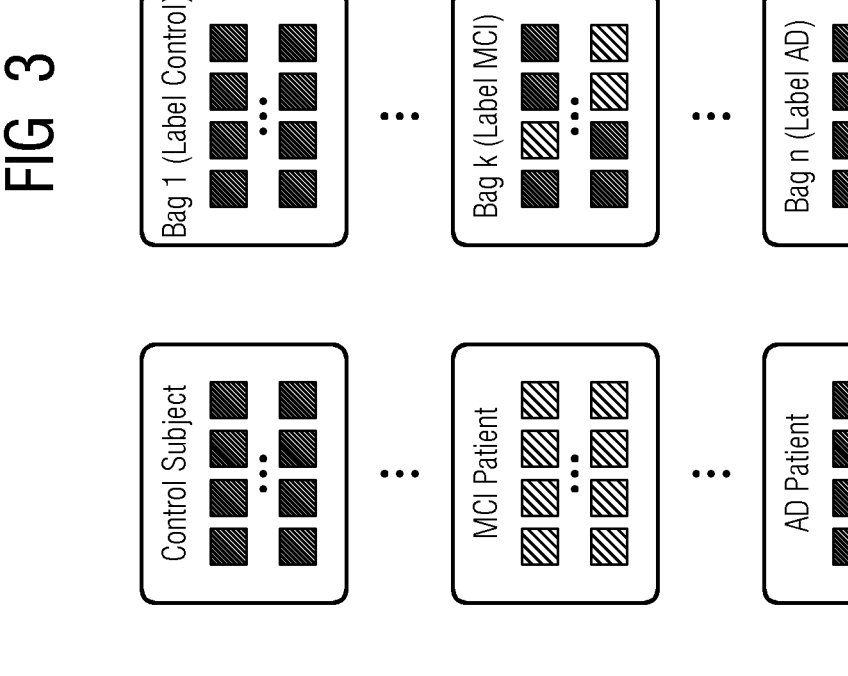

FIG. 3 shows an exemplary network architecture by using an artificial neural network, ANN, in particular, a convolutional network, CNN, of the cross-sectional processing sub-pipeline of the system, proposed herein. The proposed system is trained on image patches rather than on the whole image. This is based on the technical assumption that local patches contain disease-related information that can be extracted by the ANNs. The system takes a group of multi-modal 3D patches as input and predicts whether they are extracted from a control group (healthy person), a patient with mild cognitive impairment, MCI or, a patient with Alzheimer's disease, AD.

To train such a network, for each subject, the PET images are first registered to the structural MRI images and then multi-modal 3D patches in the brain are extracted. The labels (controls, MCI or AD) are assigned to all the patches extracted from the corresponding subject. A CNN is then trained to classify patches according to their labels. One advantage of such a patch-based design is that the network can evaluate the amount of predictive information for each patch, which can provide valuable information for interpretation.

Since all stages of AD are targeted and patches from the whole brain (including non-AD regions) are sampled or scanned, it is likely that a relatively small proportion of the sampled patches will contain disease-related features, causing an imbalance between positive and negative samples in CNN training. To overcome this issue, MIL is used. Instead of treating patches as individual samples, MIL reorganizes training patches into "bags" corresponding to subjects in the training dataset, with each bag assigned a label. A bag may be construed as set or group. A bag is different from a patch. In our case, we only mix patches from controls with that of MCI or AD patients. If one of the patches in the bag are from the disease group (MCI or AD), its label is assigned to the corresponding disease group; otherwise, it is labeled as control. One advantage of MIL is that it can pick out the most indicative samples from a pool of mixed samples, which fits the task where the model will learn to identify disease-related features when their proportion is low.

In a phase, after the training, the model will be applied to patches sampled from Cartesian grid with interval equal to half of the patch size to obtain predictions of class membership of all the patches. The average predictions will be used to determine the subject-level class prediction. In addition, the model output of individual patches can be resampled into a heatmap indicating the most informative region to better interpret the rational of the final result or decision.

Figure 4:
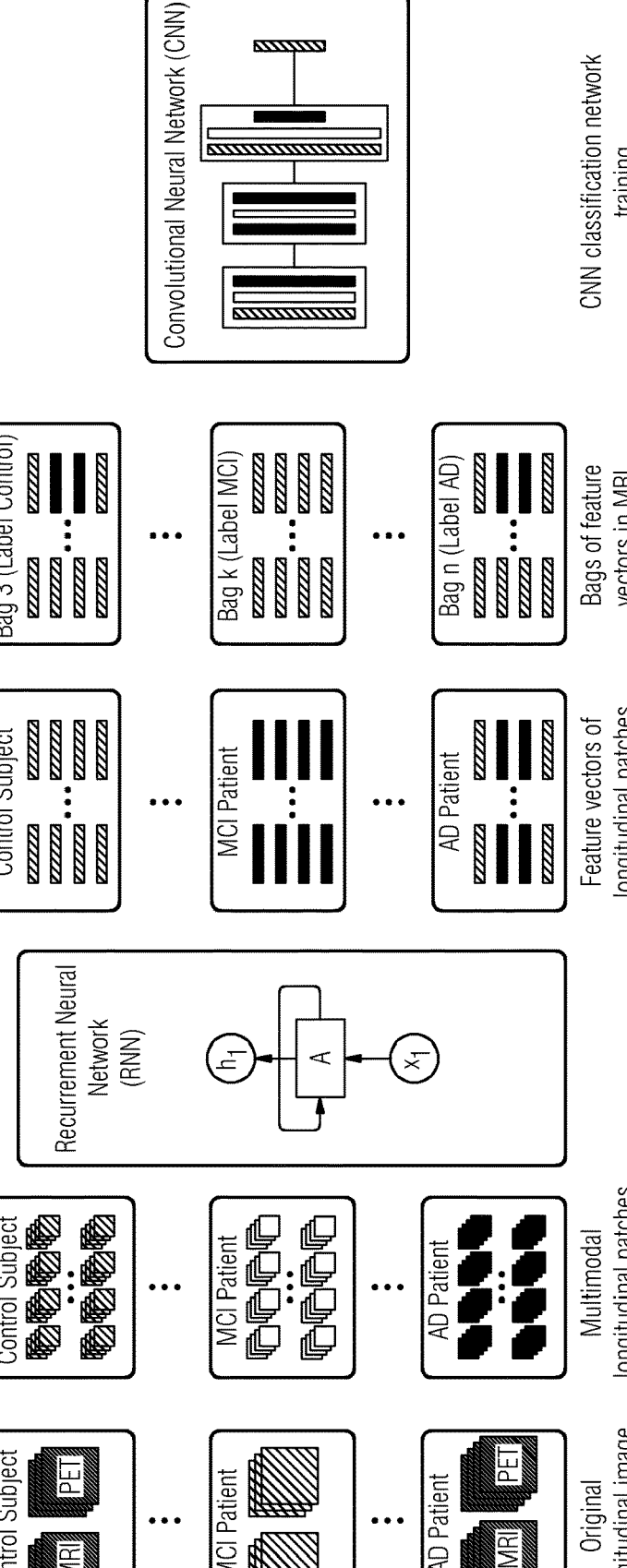
FIG. 4 shows an example longitudinal sub-pipeline in a schematic representation.

For the longitudinal setting, i.e., multiple multi-modal scans (also denoted as images) of the same subject are available and processed, the corresponding longitudinal sub-pipeline is illustrated in FIG. 4.

The longitudinal sub-pipeline includes at least the following acts:

(1) First, a highly regularized deformable registration will be performed to register each of the follow-up MRI scans to the baseline one to establish voxel-wise cor-respondence. The longitudinal sub-pipeline does not directly extract volume change from the deformation field as conventionally done. Instead, acts (2) to (4) are executed.

(2) For each patch of interest in baseline (BasePAT), we identify the corresponding patch in each of the follow-up MRI images using the deformation field. These patches are extracted in their native or original image space of each longitudinal image to join a series of corresponding longitudinal patches (one series for each BasePAT). By doing this, image information is maximally preserved because no smoothing or resampling are performed.

(3) These longitudinal patches will then be fed to a recurrent neural network (RNN) (e.g., see reference [7]) to generate a feature vector with longitudinal disease information. One advantage of RNN is that it can handle data with varying number of timepoints.

(4) Similar to the cross-sectional sub-pipeline, these feature vectors from different patches of different subjects will then be grouped into bags for MIL training to predict class membership of the corresponding patch series.

The inference process is similar to that of the cross-section sub-pipeline (FIG. 3). The only difference is that the input to the longitudinal pipeline (FIG. 4) is longitudinal patches (obtained the same way as in the training) rather than cross-sectional ones.

The outputs of the longitudinal pipeline are the prediction of class membership and heatmap indicating the most informative regions.

It is to be noted, although the proposed AI system is described here in the context of structural MRI and amyloid PET images for AD staging, it can be applied to other classification problem by modifying the loss function.

Alternative Embodiments:

Instead of sampling patches from the whole brain, the AI system can focus on brain regions associated with AD, e.g., including tau related regions (temporal lobe, parietal lobe, brain stem) and amyloid related regions (temporobasal and frontomedial areas).

Another alternative embodiment is to employ multi-resolution patches rather than fixing patch size, which allows integration of information at different scales.

Figures 5, 6:
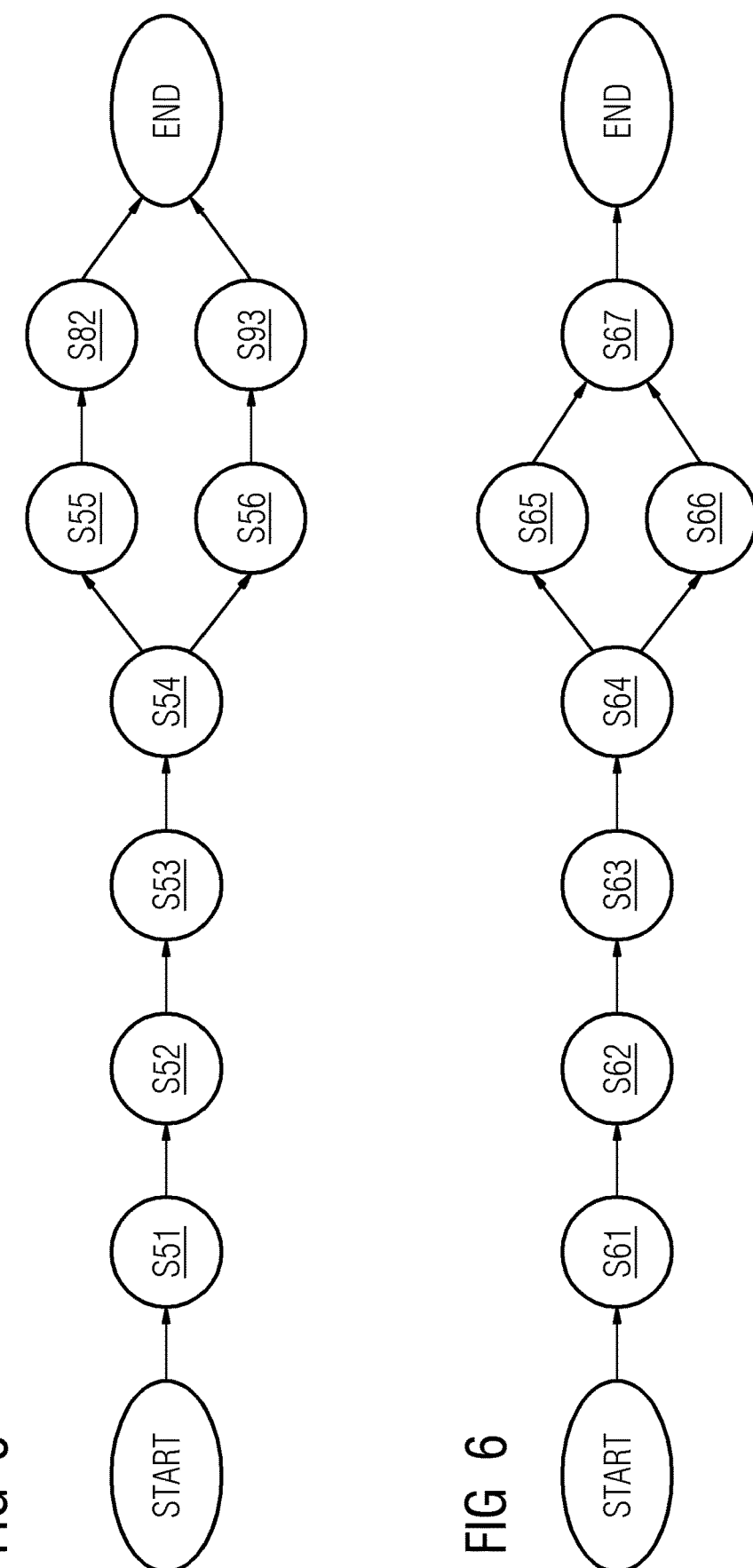
FIG. 5 shows a workflow for a training method according to an embodiment.
FIG. 6 depicts a workflow for an inference method according to an embodiment.

FIG. 5 is a flowchart for a training method. After start of the method, in act S51, the images are received. In act S52, the images are registered, which have been received in the act before. In act S53, a multi-modal dataset mmd is generated. The multi-modal dataset mmd includes at least the received images and a transformation dataset T, representing a transformation between these (received) images. In act S54, multi-modal image patches are extracted in the space of the originally received image. In act S55, a cross-sectional pipeline is provided for processing cross-sectional imaging data, and, in act S56, a longitudinal pipeline is provided for processing longitudinal imaging data.

In this context, it is to be noted, that the terms "pipeline" and "sub-pipeline" are used in this document as synonyms.

The sequence of the acts of the method is not limited to the given sequence. For example, it is possible to change the acts S56 and S55, so that first S56 is executed and subsequently S55 or the acts may be executed in parallel.

In act S82, the first ANN, namely the CNN, is provided. In act S93 the second ANN, namely the RNN, is provided.

FIG. 6 shows a flowchart of an interference method, to be used in an inference phase, after the networks have been trained and/or tested. After having started the method, in act S61, the images are received, in particular as a pair of images from two different modalities, in particular as an MRI image and a PET image. In act 62, the images are registered. The images are registered differently for the cross-sectional sub-pipeline and for the longitudinal sub-pipeline. In act S63, the multi-modal dataset mmd is generated. In act S64, multi-modal image patches are extracted in the space of the images, originally received. In act S65, a cross-sectional sub-pipeline is provided for processing cross-sectional imaging data, and, in act S66, a longitudinal sub-pipeline is provided for processing longitudinal imaging data. Here again, the sequence of method acts may be changed, so that first the longitudinal sub-pipeline is provided after providing the cross-sectional one or, both method acts of providing are executed in parallel.

In act S67, a result dataset r is provided or calculated as a predicted class membership [cognitively normal class or healthy person, MCI class and AD class]. The result dataset r serves as image-based biomarker for active disease progression of Alzheimer's disease and related dementias.

Figure 7:
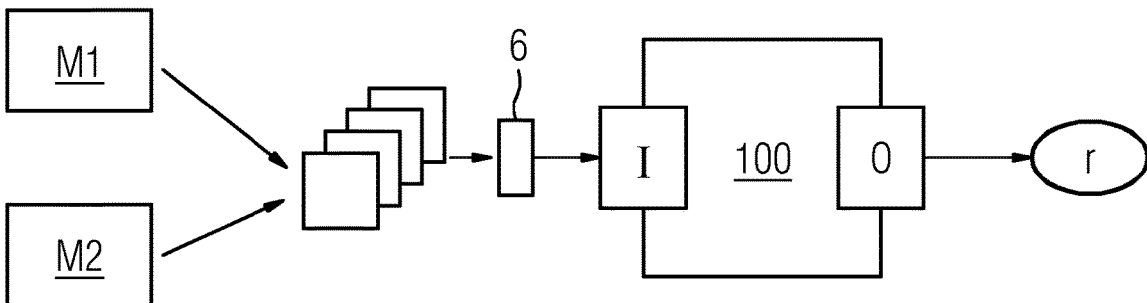
FIG. 7 shows a structural overview of a computing unit configured for executing training and/or inference according to an embodiment in a schematic representation.

FIG. 7 is a schematic representation of a computing unit 100 in an overview figure. Multiple images are acquired from at least two different modalities M1, M2 (e.g., PET and MRI). The received images are preferably pre-processed in module 6. The preprocessing may serve to generate patches and/or bags of patches. The input data (e.g., bags of patches or bags of feature vectors, both in particular in MIL, or patches) received via a reception interface I and are processed in the computing unit 100 to generate the result dataset r.

The result dataset r is provided on an output interface O. The computing unit 100 is configured for executing the acts of registering images, generating a multimodal dataset, extracting multimodal image patches, providing a first interface to a cross-sectional sub-pipeline and providing a second interface to a longitudinal sub-pipeline. The first and/or second interface may be an internal or an external interface.

Figure 8:
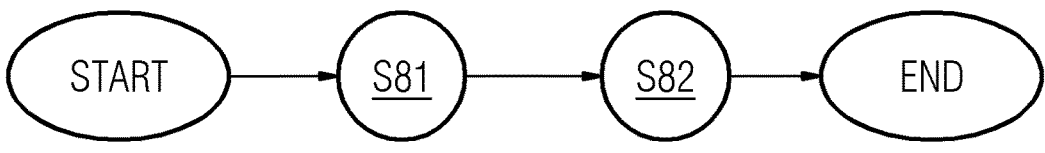
FIG. 8 is an example workflow of training for a cross-sectional sub-pipeline.

FIG. 8 is a flowchart for training the cross-sectional sub-pipeline. After having started the method, in act S81, a first ANN, in particular the CNN is trained with a patch-based multiple instance learning scheme. The patch-based multiple instance learning scheme is used for classifying the extracted multi-modal image patches by predicting a class membership (cognitively normal class, MCI class or AD class), represented in the result dataset r.

In act S82, the first trained ANN, in particular, the CNN, is provided. After this, the method may end.

Figure 9:
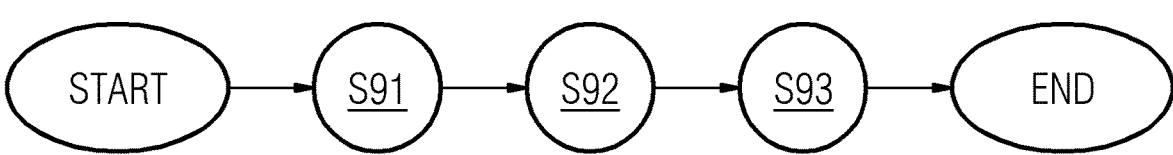
FIG. 9 is an example workflow of training method for a longitudinal sub-pipeline.

FIG. 9 shows a flowchart of training a longitudinal sub-pipeline. After having started the method, in act S91, a second ANN, in particular an RNN, is trained for generating feature vectors of longitudinal patches with longitudinal disease information. In act S92, another CNN is trained with the patch-based multiple instance learning scheme to predict a class membership in act S93, represented in the result dataset r, using the feature vectors generated by the RNN, wherein a class is selected from the group consisting of cognitively normal class, an MCI class and an AD class. After this the method may end.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of the present invention or with respect to a particular figure are, wherever applicable, also advantages of other embodiments of the present invention.

The invention claimed is:

1. A computer-implemented method for training artificial neural networks (ANNs) for generating image-based biomarkers for active disease progression of Alzheimer's disease (AD) and/or related dementias (ADRD), the method comprising:

receiving a pair of images from two different modalities of the same subject at a same timepoint, wherein a subject's imaging data is processed as cross-sectional imaging data when acquired in a cross-sectional setting in which the subject has only one pair of images acquired at the same timepoint and wherein the subject's imaging data is processed as longitudinal imaging data when the imaging data is acquired in a longitudinal setting in which the subject has multiple pairs of images received at different timepoints;

registering the images, wherein for the cross-sectional imaging data registering is performed between images at the same timepoint and wherein for the longitudinal imaging data registering is performed between images of the same subject;

generating a multi-modal dataset comprising the received images and transformations generated by the registering;

extracting multi-modal image patches in a space of the received images, either cross-sectional or longitudinal, based on the generated multi-modal dataset;

performing one of the following:

(a) processing the cross-sectional imaging data using a cross-sectional sub-pipeline that comprises training a first ANN by using a patch-based multiple instance learning (MIL) scheme for classifying the extracted multi-modal image patches by predicting a class membership, wherein a class is selected from the group consisting of cognitively normal class, mild cognitive impairment class (MCI class), and Alzheimer Disease class (AD class); or (b) processing the longitudinal imaging data using a longitudinal sub-pipeline that comprises training a second ANN for generating feature vectors of longitudinal patches with longitudinal disease information, and training a third ANN with the patch-based MIL scheme to predict a class membership using the feature vectors generated by the second ANN, wherein a class is selected from the group consisting of cognitively normal class, MCI class and AD class; and providing for generating image-based biomarkers for active disease progression of Alzheimer's disease and related dementias, ADRD, the trained first ANN if the cross-sectional imaging data was processed or the trained second ANN and the trained third ANN if the longitudinal imaging data was processed.

2. The method according to claim 1, wherein cross-entropy loss is used as loss function in the training.

3. The method according to claim 1, wherein, when training the first ANN and/or the third ANN, the patch-based MIL scheme re-organizes the patches into bags and assigns a class or a label to each bag, wherein the class is selected from the group consisting of cognitively normal class, MCI class and AD class.

4. The method according to claim 1, wherein the trained first, second, and/or third ANN are trained on patches.

5. The method according to claim 1, wherein, the longitudinal sub-pipeline does not directly extract volume change from a deformation field.

6. An inference method for generating image-based biomarkers for active disease progression of Alzheimer's disease (AD) and/or related dementias (ADRD), the inference method comprising:

receiving a pair of images from two different modalities of a same subject at a same timepoint, wherein a subject's imaging data is processed as cross-sectional imaging data when acquired in a cross-sectional setting in which the subject has only one pair of images acquired at the same timepoint, and wherein the subject's imaging data is processed as longitudinal imaging data when the imaging data is acquired in a longitudinal setting in which the subject has multiple pairs of images received at different timepoints;

registering the images, wherein for cross-sectional imaging data registering is performed between the images at the same timepoint and wherein for longitudinal imaging data registering is performed between the images of the same subject;

generating a multi-modal dataset comprising the received images and the transformations generated by the registrations;

extracting multi-modal image patches in a space of the received images based on the generated multi-modal dataset;

performing one of the following:

(a) processing the cross-sectional imaging data using a cross sectional sub pipeline that comprises using a first trained artificial neural network (ANN) system, which was trained with a multiple instance learning (MIL) scheme for classifying the extracted multimodal images patches by predicting a class membership, wherein a class is selected from the group consisting of cognitively normal class, mild cognitive impairment (MCI) class, and Alzheimer Disease (AD) class; or (b) processing the longitudinal imaging data using a longitudinal sub pipeline that comprises using a second ANN system trained to generate feature vectors of longitudinal patches with longitudinal disease information, and using a third ANN to predict a class membership from the feature vectors, wherein a class is selected from the group consisting of cognitively normal class, MCI class and AD class; and providing the predicted class membership as result dataset on an output interface, wherein the result dataset serves as image-based biomarker for active disease progression of the AD and/or ADRD.

7. The inference method according to claim 6, wherein a heatmap is provided as the result dataset on the output interface in addition to the predicted class membership.

8. The inference method according to claim 6, wherein processing the cross-sectional imaging data comprises:

registering the images of a first modality of the different modalities with the corresponding images of a second modality of the different modalities from the same subject at the same timepoint to generate the multi-modal dataset;

using the first trained ANN to assign a class label for each of the extracted patches;

using average predictions of all the patches to determine a subject-level class prediction; and assembling model outputs of all individual patches into a heatmap indicating the most informative region for the prediction, serving as evidence for interpretation.

9. The inference method according to claim 6, wherein, when processing the longitudinal imaging data, the longitudinal sub-pipeline executes:

registering the images of a first modality of the different modalities with the corresponding images of a second modality of the different modalities from the same subject at each of the different timepoints;

registering the images of the first timepoint of the different timepoints to the other timepoints of the different timepoints from the same subject;

generating the multi-modal dataset of received images and a transformation dataset generated by the registrations;

extracting the multi-modal patches from the first timepoint of the multi-modal dataset as baseline patches;

identifying corresponding patches of the other timepoints in the multi-modal datasets for each baseline patch using a corresponding transformation derived from registration;

extracting spatially corresponding patches in their original image space of the images from each timepoint, including the first and other timepoints, to generate a series of longitudinal images patches for each subject as one series for each baseline patch;

feeding the patches stemming from the longitudinal images to the trained second ANN to generate the feature vectors with longitudinal disease information;

feeding the feature vector to the third ANN to generate class prediction;

using average predictions of all the baseline patches to determine subject-level class prediction; and assembling model outputs of all individual patches into a heatmap indicating the most informative region for the prediction, serving as evidence for further processing.

10. The inference method according to claim 6, wherein the second ANN comprises an RNN.

11. The inference method according to claim 6, wherein the first ANN comprises a first convolutional neural network, and wherein the third ANN comprises a third convolutional neural network.

12. A system for generating image-based biomarkers for active disease progression of Alzheimer's disease (AD) and/or related dementias (ADRD), the system comprising:

a reception interface configured to receive a pair of images from two different modalities of the same subject at a same timepoint, wherein the images are processed as cross-sectional imaging data when acquired in a cross-sectional setting in which the pair of images is acquired at the same timepoint and wherein is the images are processed as longitudinal imaging data when acquired in a longitudinal setting in which the pair of images is received with other pairs of images received at different timepoints; and a processor configured to:

register the images, wherein, for the cross-sectional imaging data, registering is performed between the images at the same timepoint, and, wherein, for the longitudinal imaging data, registering is performed between the images of the same subject;

generate a multi-modal dataset comprising the received images and transformations generated by the registrations;

extracting multi-modal image patches in a space of the received images based on the generated multi-modal dataset;

provide a first interface to a cross-sectional sub-pipeline for processing cross-sectional imaging data or provide a second interface to a longitudinal sub-pipeline for processing longitudinal imaging data; wherein the cross-sectional sub-pipeline for processing cross-sectional imaging data comprises using a first trained artificial neural network (ANN) system trained to classify the extracted multi-modal images patches by prediction of a class membership, wherein the class membership is selected from a cognitively normal class, mild cognitive impairment (MCI) class, and AD class; wherein the longitudinal sub-pipeline for processing longitudinal imaging data comprises using a second trained ANN system trained to generate feature vectors of longitudinal ones of the multi-modal image patches with longitudinal disease information, and using a third trained ANN to predict the class membership from the feature vectors; and an output interface configured to provide the predicted class membership as result dataset, wherein the result dataset serves as the image-based biomarkers for disease progression of AD and/or ADRD.

13. The system according to claim 12 wherein the first ANN comprises a first convolutional neural network (CNN), and wherein the third ANN comprises a third CNN.

14. The system according to claim 12 wherein the second ANN comprises a recurrent neural network.

15. The system according to claim 12, wherein a heatmap is provided as the result dataset on the output interface in addition to the predicted class membership.

\* \* \* \* \*